United States Patent
Tass et al.

(10) Patent No.: US 10,617,869 B2
(45) Date of Patent: Apr. 14, 2020

(54) DEVICE FOR EFFECTIVE INVASIVE DESYNCHRONIZING NEUROSTIMULATION

(71) Applicant: Forschungszentrum Juelich GmbH, Juelich (DE)

(72) Inventors: Peter Alexander Tass, Juelich (DE); Oleksandr Popovych, Dueren (DE); Markos Xenakis, Athens (GR)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 253 days.

(21) Appl. No.: 15/521,983

(22) PCT Filed: Oct. 30, 2015

(86) PCT No.: PCT/EP2015/075287
§ 371 (c)(1),
(2) Date: Apr. 26, 2017

(87) PCT Pub. No.: WO2016/071234
PCT Pub. Date: May 12, 2016

(65) Prior Publication Data
US 2018/0280697 A1     Oct. 4, 2018

(30) Foreign Application Priority Data
Nov. 3, 2014    (DE) .................. 10 2014 115 994

(51) Int. Cl.
*A61N 1/36* (2006.01)
*A61N 5/06* (2006.01)
(Continued)

(52) U.S. Cl.
CPC ...... *A61N 1/36125* (2013.01); *A61B 5/04001* (2013.01); *A61B 5/4836* (2013.01);
(Continued)

(58) Field of Classification Search
CPC ............ A61N 1/36125; A61N 1/36139; A61N 1/025; A61N 5/0622; A61N 1/3605;
(Continued)

(56) References Cited

U.S. PATENT DOCUMENTS

| 2010/0331912 | A1 | 12/2010 | Tass et al. |
| 2011/0201977 | A1 * | 8/2011 | Tass .................... A61H 7/004 601/15 |

(Continued)

FOREIGN PATENT DOCUMENTS

| DE | 10 2007 051 847 A1 | 5/2009 | |
| DE | 10 2012 002 437 A1 | 8/2013 | |
| DE | 102012002437 A1 * | 8/2013 | ......... A61N 1/36064 |

OTHER PUBLICATIONS

A neuronal learning rule for sub-millisecond temporal coding, Wulfram Gerster, Richard Kempter, Letters to Nature, vol. 383; Sep. 5, 1996.
(Continued)

*Primary Examiner* — Carl H Layno
*Assistant Examiner* — James Moss
(74) *Attorney, Agent, or Firm* — Lowe Graham Jones PLLC; Bruce E. Black

(57) ABSTRACT

A device that suppresses a pathological synchronous and oscillatory neuron activity, and includes a non-invasive stimulation unit implantable in a patient, for stimulation, using electrical and/or optical stimuli, of neurons in the patient's brain and/or spinal cord, where those neurons are showing pathologically synchronous and oscillatory neuron activity, and the stimuli are deigned to suppress are this activity when administered to the patient. Moreover, a measuring unit records measurement signals reflecting the neuron activity of the stimulated neurons and a control and analysis unit controls the stimulation unit to administer stimuli, check the success of stimulation based on the
(Continued)

measurement, and, if the stimulation success is not sufficient, insert one or more stimulation breaks in the application of the stimuli or extend one or more stimulation breaks, where no stimuli that could suppress the pathological synchronous and oscillatory neuron activity are applied during the stimulation breaks.

20 Claims, 7 Drawing Sheets

(51) Int. Cl.
*A61B 5/00* (2006.01)
*A61B 5/04* (2006.01)
*A61N 1/02* (2006.01)
*A61N 5/067* (2006.01)
*A61N 1/05* (2006.01)

(52) U.S. Cl.
CPC ............ *A61N 1/025* (2013.01); *A61N 1/3605* (2013.01); *A61N 1/36139* (2013.01); *A61N 1/36178* (2013.01); *A61N 5/0622* (2013.01); *A61N 1/0551* (2013.01); *A61N 1/36064* (2013.01); *A61N 1/36067* (2013.01); *A61N 1/36082* (2013.01); *A61N 1/36096* (2013.01); *A61N 1/36103* (2013.01); *A61N 1/36135* (2013.01); *A61N 2005/067* (2013.01); *A61N 2005/0612* (2013.01); *A61N 2005/0629* (2013.01); *A61N 2005/0651* (2013.01)

(58) Field of Classification Search
CPC ........ A61N 1/36178; A61N 2005/0629; A61N 1/36096; A61N 2005/0612; A61N 1/0551; A61N 2005/067; A61N 2005/0651; A61N 1/36135; A61N 1/36103; A61N 1/36082; A61N 1/36067; A61N 1/36064; A61B 5/04001; A61B 5/4836
See application file for complete search history.

(56) References Cited

U.S. PATENT DOCUMENTS

| 2012/0197338 | A1* | 8/2012 | Su | A61N 1/36167 |
| | | | | 607/41 |
| 2013/0090519 | A1 | 4/2013 | Tass et al. | |
| 2013/0190663 | A1 | 7/2013 | Tass et al. | |
| 2015/0018898 | A1* | 1/2015 | Tass | A61N 1/36064 |
| | | | | 607/62 |

OTHER PUBLICATIONS

Chemical Oscillations, Waves, and Turbulence, Y. Kuramoto, Chapter 5.
Classics in the History of Psychology, "A Contribution to Experimental Psychology", Hermann Ebbinghaus, Chapters 1, 6 and 8.
Adamchic et al., Coordinated Reset Neuromodulation for Parkinson's Disease, Movement Disorders, vol. 29, No. 13, 2014, pp. 1679-1684.
Tass etl al. Coordinated reset neuromodulation has sustained aftereffects in parkinsonian monkeys, Annals of Neurology 72, 816-820 (2012).
Temperli et al., How do parkinsonian signs return after discontinuation of subthalamic DBS? Neurology 60, pp. 78-81 (2003).
Long-term anti-kindling effects of desynchronizing brain stimulation. a theoreticastudy, Peter AS. Tass, Milan Majtanik, Biol. Cybern (2006) 94: pp. 58-66.
Malleability of Spike-Timing-Dependent Plasticity at the CA3-CA1 Synapse, Gayle M. Wittenberg and Samuel S.-H. Wang, The Journal of Neuroscience, Jun. 14, 2006, 26(24), pp. 6610-6617.
Spike Timing-Dependent Plasticity: A Hebbian Learning Rule, Natalia Caporale and Yang Dan, Annu.Rev. Neurosci, 2008, 31: pp. 25-46.
Spike-timing-dependent plasticity: common themes and divergent vistas, Adam Kepecs, Mark C.W. von Rossum, Biiol, Cybern. 87, pp. 446-458 (2002.
Synaptic Modifications in Cultured Hippocampal Neurons: Dependence on Spike Timing, Synaptic Strength, and Postsynaptic Cell Type, Guo-qiang Bi and Mu-ming Poo, The Journal of Neuroscience, Dec. 1998, 18(24): pp. 10464-10472.
PCT/EP2014/075287 International Search Report dated Jan. 28, 2016.

* cited by examiner

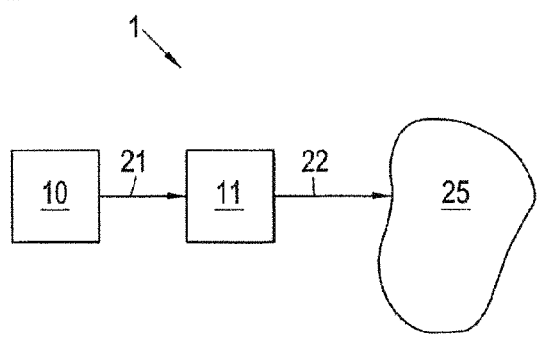
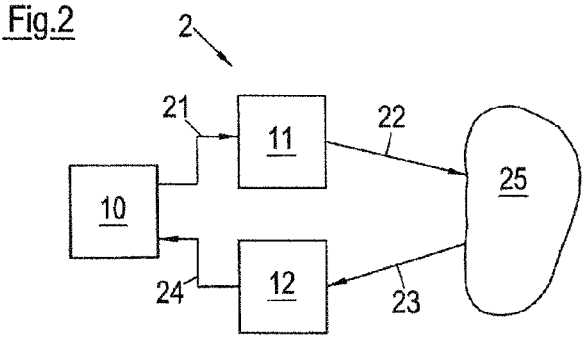

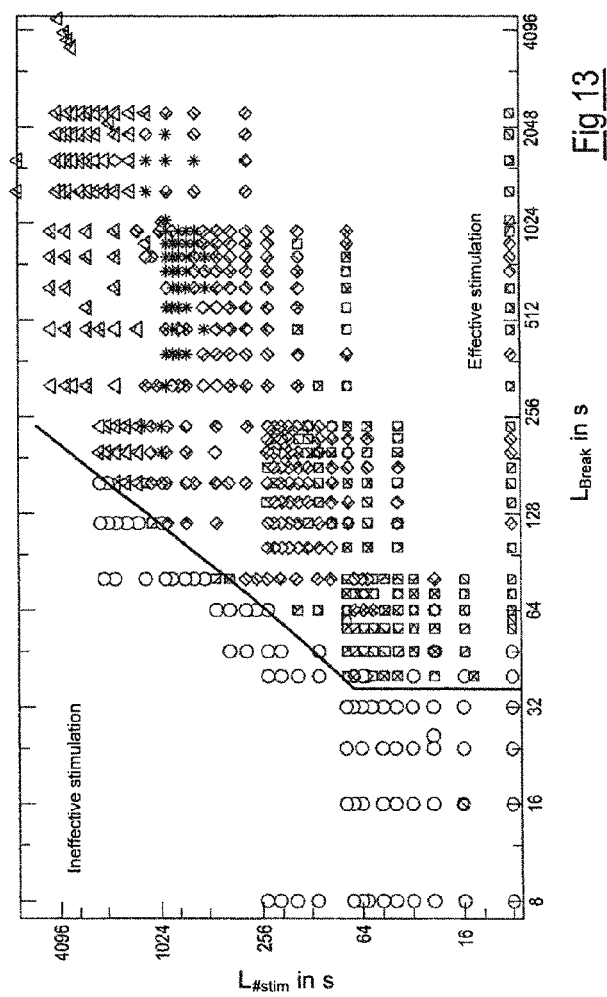

DEVICE FOR EFFECTIVE INVASIVE DESYNCHRONIZING NEUROSTIMULATION

CROSS-REFERENCE TO RELATED APPLICATIONS

This application is a National Stage entry of International Application No. PCT/EP2015/075287, filed Oct. 30, 2015, which claims priority to German Patent Application No. 10 2014 115 994.2 filed Nov. 3, 2014, the disclosures of these priority applications are incorporated in their entirety herein by reference.

TECHNICAL FIELD

The invention relates to an apparatus and to a method for effective invasive desynchronizing neurostimulation.

BACKGROUND

Nerve cell assemblies in the circumscribed regions of the brain are pathologically, e.g. excessively synchronously, active in patients with neurological or psychiatric diseases such as Parkinson's disease, essential tremor, epilepsy, functional disturbances after a stroke, dystonia or obsessive compulsive disorders. In this case, a large number of neurons synchronously form action potentials, i.e. the participating neurons fire excessively synchronously. In a healthy person, in contrast, the neurons fire with a different quality, i.e. in an uncorrelated manner, in these brain sectors.

In Parkinson's disease, the pathologically synchronous activity changes the neuronal activity in other brain regions, e.g. in areas of the cerebral cortex such as the primary motor cortex. In this respect, the pathologically synchronous activity in the region of the thalamus and of the basal ganglia, for example, imposes its rhythm on the cerebral cortex areas such that ultimately the muscles controlled by these areas develop pathological activity, e.g. a rhythmic trembling (tremor).

Deep brain stimulation is used to treat Parkinson's patients who cannot be sufficiently treated by medication. In this process, deep electrodes are implanted in specific areas of the brain, e.g. in the subthalamic nucleus. An electrical stimulation is carried out via the deep electrodes to relieve the symptoms. With the standard high-frequency stimulation for treating Parkinson's disease, a so-called high-frequency permanent stimulation is carried out at frequencies of more than 100 Hz. This type of treatment has no long-lasting therapeutic effects (cf. P. Temperli, J. Ghika, J.-G. Villemure, P. Burkhard, J. Bogousslaysky, and F. Vingerhoets: How do Parkinsonian signs return after discontinuation of subthalamic DBS? Neurology 60, 78 (2003)). "Coordinated reset stimulation" (CR stimulation), that can additionally have long-lasting therapeutic effects, manages with less stimulus current (P. A. Tass, L. Qin, C. Hauptmann, S. Doveros, E. Bezard, T. Boraud, W. G. Meissner: Coordinated reset neuromodulation has sustained after-effects in Parkinsonian monkeys. Annals of Neurology 72, 816-820 (2012); I. Adamchic, C. Hauptmann, U. B. Barnikol, N. Pawelcyk, O. V. Popovych, T. Barnikol, A. Silchenko, J. Volkmann, G. Deuschl, W. Meissner, M. Maarouf, V. Sturm, H.-J. Freund, P. A. Tass: Coordinated Reset Has Lasting Aftereffects in Patients with Parkinson's Disease. Movement Disorders (published online, 2014)).

With other diseases, e.g. epilepsy that cannot be sufficiently treated with medication, different electrodes, e.g. epicortical or epidural electrodes, are also implanted in addition to deep electrodes. With further diseases, e.g. chronic pain syndromes, it is customary to stimulate the spinal cord not only by means of deep electrodes in the brain, but also by means of e.g. epidural electrodes. In contrast to CR stimulation, most other types of stimulation have no long-lasting therapeutic effects.

Therapeutic effects can also be achieved by direct stimulation of the brain tissue or spinal cord by light, e.g. via implanted light-guides. Different spatiotemporal stimulation patters such as CR stimulation can also be used in this respect.

Limitations can arise in the conventional treatment of brain diseases and spinal cord diseases in which electrodes or light-guides or comparable stimulation units are implanted in the brain and/or spinal cord of the patient to achieve therapeutic effects by an electrical and/or optical stimulation of the brain tissue or of the spinal cord. Such stimulation treatments can cause side effects, e.g. due to the unwanted stimulation of adjacent structures as a result of the propagation of stimulus currents or due to the simultaneous stimulation, which is difficult to avoid for anatomical reasons, of e.g. fibrous webs and/or fibers that run in the vicinity of the target region or even through the target region. Such situations result e.g. due to the characteristic close anatomical proximity of the target point targeted in the electrode implantation and of other anatomic structures (whose stimulation results in side effects), due to special individual anatomical conditions (e.g. in the sense of the location of blood vessels that have to be spared on the implantation of the electrodes) or also due to suboptimal or even erroneous electrode implantation.

For example, side effects can occur due to unfavorably positioned electrodes that only disappear when the stimulation level is reduced so much that the desired effects do not occur to a sufficient degree or do not even occur at all. Analogously, an insufficient stimulation effect cannot be compensated by an increase in the stimulation intensity by any desired amount since hereby side effects typically occur or even damage to the tissue is caused. Where necessary, badly positioned electrodes or other stimulation units have to be re-implanted to position them such that the treatment is efficient. A repeat implantation is always associated with a risk, e.g. due to an injury to vessels or due to an infection.

SUMMARY

It is the underlying object of the invention to provide an apparatus and a method that allow good, and in particular long-lasting, therapeutic effects by stimulation with highly minimal stimulus levels.

The object underlying the invention is satisfied by the features of the independent claims. Advantageous further developments and aspects of the invention are set forth in the dependent claims.

BRIEF DESCRIPTION OF DRAWINGS

The invention will be described in more detail in the following in an exemplary manner with reference to the drawings. There are shown in these:

FIG. 1 illustrates a schematic representation of an apparatus for suppressing a pathologically synchronous and oscillatory neuronal activity and in particular for desynchronizing neurons having a pathologically synchronous and oscillatory activity in accordance with a first embodiment;

FIG. 2 illustrates a schematic representation of an apparatus for suppressing a pathologically synchronous and oscillatory neuronal activity and in particular for desynchronizing neurons having a pathologically synchronous and oscillatory activity in accordance with a second embodiment;

FIG. 13 illustrates a diagram for representing the effectiveness of CR stimulations having different stimulation phase lengths and stimulation break lengths.

DETAILED DESCRIPTION

Figure 3:
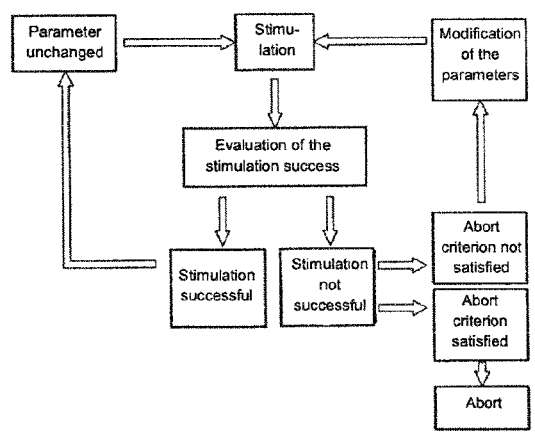
FIG. 3 illustrates a flowchart for illustrating a regulation of the lengths of stimulation phases and stimulation breaks in accordance with a first variant.

An apparatus 1 for stimulating neurons having a pathologically synchronous and oscillatory neuronal activity is shown schematically in FIG. 1. The apparatus 1 comprises a control and analysis unit 10 and a stimulation unit 11. During the operation of the apparatus 1, the control and analysis unit 10 carries out a control of the stimulation unit 11. For this purpose, the control and analysis unit 10 generates control signals 21 which are received by the stimulation unit 11.

The stimulation unit 11 is surgically implanted in the body of the patient and generates electrical and/or optical stimuli 22 on the basis of the control signals 21 which are administered to the brain and/or to the spinal cord 25 of the patient. The stimuli 22 are adapted to suppress the pathologically synchronous and oscillatory neuronal activity on administration to the patient and in particular to desynchronize the neurons having the pathologically synchronous and oscillatory activity.

The control and analysis unit 10 can be a non-invasive unit, i.e. it is located outside the body of the patient during the operation of the apparatus 1 and is not surgically implanted in the body of the patient.

During the operation of the apparatus 1, the efficiency of the stimulation can be improved at low stimulus levels, if an insufficient stimulation effect is determined, by the introduction of stimulation breaks by, for example, the physician or by the user. No application of stimuli that could suppress the pathologically synchronous and oscillatory neuronal activity takes place during the stimulation breaks. It is, however, conceivable that different stimuli that are not adapted to suppress pathologically synchronous and oscillatory neuronal activity are applied during the stimulation breaks, in particular using the stimulation unit 11. In accordance with a further embodiment, stimulation of any kind with the aid of the stimulation unit 11 is dispensed with during the stimulation breaks. The above-described stimulation breaks can furthermore be added, e.g. in the case of side effects and/or of unfavorably positioned electrodes, to allow an efficient stimulation at low stimulus levels. The length of the stimulation breaks can be kept constant, can be set by the physician or user or can be regulated as described further below.

The invention utilizes a counter-intuitive relationship. The smaller the success achieved by the weak stimulation, the longer the breaks inserted into the stimulation procedure. It can in particular be brought about by the introduction of such breaks that an otherwise ineffective stimulation is effective.

The counter-intuitive mechanism underlying the invention can be made plausible by the following considerations. As a result of synaptic plasticity, assemblies of neurons are very plastic, i.e. they can be present in a plurality of different stable states. E.g. in states with a low mean synaptic connection strength and asynchronous neuronal activity, i.e. the neurons fire in an uncorrelated manner, or in states with a highly pronounced mean synaptic connection strength and synchronous neuronal activity, i.e. the neurons fire in a correlated manner, e.g. in time, that is coincident. There are typically a plurality of stable states having an intermediate mean synaptic connection strength and an intermediate pronounced state of the neuronal synchronization between these two extremes. Multistability in the mathematical sense is therefore present.

The invention utilizes the surprising fact that the system, i.e. the stimulated neural ensemble, can be pushed from one attractor (stable state) to the next even with a low stimulation if there is a sufficiently long break between the stimulation phases during which the system is spontaneously pulled into the new attractor (i.e. without stimulation), which would not be possible under stimulation. The system moves so-to-say stepwise from highly synchronous attractors to increasingly weaker synchronous attractors due to the portioned stimulation.

The introduction of sufficiently long stimulation breaks allows an efficient stimulation at low stimulation levels. The stimulation level can then be smaller by a factor of 2 to 3 than the minimum stimulation level that results in a long-lasting desynchronization with permanent stimulation, i.e. with a stimulation without the stimulation breaks described herein. The stimulus level of the stimulation in accordance with the invention with stimulation breaks can in particular be in a range from ⅓ of the minimum stimulus level up to ⅔ of the minimum stimulus level that results in a long-lasting desynchronization on a permanent stimulation without the stimulation breaks in accordance with the invention.

The length of a stimulation break between two consecutive stimulation sections can amount to at least 3 minutes, but can also be substantially longer and can, for example, amount to at least 5 minutes or at least 10 minutes or at least 20 minutes or at least 30 minutes or at least 1 hour or at least 2 hours or at least 3 hours. To achieve first effects, the stimulation break length has to correspond to at least 200 periods of the oscillation to be desynchronized. A pronounced desynchronization can only be achieved from approximately 1,000 up to even 22,000 periods. In the case of a delta oscillation at a frequency in the range from 1 to 4 Hz, the period length amounts e.g. to 500 ms at 2 Hz. I.e. good effects result with breaks in the minute range or even in the hour range (1,000 to 22,000 periods then correspond to approximately 8.3 min or 3 hours). The period of pathological oscillation can for example be measured at the patient; but textbook values or experience values can also be used.

The length of the stimulation phases in which a stimulation takes place can furthermore preferably be set in addition to the length of the stimulation breaks to improve the efficiency of the stimulation at low stimulation levels. The length of the stimulation phases can be kept constant in the same manner as the length of the stimulation breaks, can be set by the physician or user or can be regulated as described further below.

The stimulation breaks can preferably be extended with too small a stimulation effect and the stimulation phases can likewise be extended.

The stimulation breaks and stimulation phases can, for example, each be of equal length and can thus increase equally. The stimulation phases can furthermore also be shorter at the start than the stimulation breaks and can increase disproportionately with too small a stimulation effect. Furthermore, any suitable other relation between the duration of the stimulation breaks and the duration of the stimulation phases can be set.

An apparatus 2 for stimulating neurons having a pathologically synchronous and oscillatory neuronal activity is shown schematically in FIG. 2. The apparatus 2 represents a further development of the apparatus 1 shown in FIG. 1. The apparatus 2, just like the apparatus 1, has a control and analysis unit 10 and a stimulation unit 11. During the operation of the apparatus 1, the control and analysis unit 10 carries out a control of the stimulation unit 11. For this purpose, the control and analysis unit 10 generates control signals 21 which are received by the stimulation unit 11.

As described above, the stimulation unit 11 is surgically implanted in the body of the patient and generates electrical and/or optical stimuli 22 on the basis of the control signals 21 which are administered to the brain and/or to the spinal cord 25 of the patient.

The apparatus 2 furthermore comprises a measuring unit 12. The stimulation effect achieved by the stimuli 22 is measured with the aid of the measuring unit 12. The measuring unit 12 records one or more measured signals 23 measured at the patient, converts them as required into electrical signals 24 and supplies them to the control and analysis unit 10. The neuronal activity in the stimulated target zone or in a zone associated with the target zone can in particular be measured by means of the measuring unit 12, with the neuronal activity of this zone correlating sufficiently closely with the neuronal activity of the target zone. A non-neuronal activity, e.g. a muscular activity, or the activation of the autonomous nervous system can also be measured by means of the measuring unit 12 provided that they are sufficiently closely correlated with the neuronal activity of the target region.

The measuring unit 12 includes one or more sensors that in particular make it possible to demonstrate a decrease or increase in the amplitude of the pathological oscillatory activity.

Non-invasive sensors can be used as the sensors, e.g. electroencephalograph (EEG) electrodes, magnetic encephalograph (MEG) sensors and sensors for measuring local field potentials (LFPs). The neuronal activity can also be determined indirectly by measurement of the associated muscular activity by means of electromyography (EMG) or indirectly by measuring the activation of the autonomous nervous system by means of measuring the skin resistance.

Alternatively, the sensors can be implanted in the body of the patient. Epicortical electrodes, deep brain electrodes for the measurement of e.g. local field potentials, subdural or epidural brain electrodes, subcutaneous EEG electrodes and subdural or epidural spinal cord electrodes can, for example, serve as invasive sensors. The deep electrodes for measuring the local field potentials can also be combined construction-wise or can even be identical to the deep electrodes used for the stimulation.

The control and analysis unit 10 processes the signals 24, e.g. the signals 24 can be amplified and/or filtered, and analyzes the processed signals 24. The control and analysis unit 10 in particular controls the stimulation unit 11 with reference to the results of this analysis. The control and analysis unit 10 can include e.g. a processor (e.g. a microcontroller) for carrying out its work.

The control and analysis unit 10 checks the stimulation success with reference to the measured signals recorded in response to the application of the stimuli and sets the stimulation parameters, in particular the lengths of the stimulation breaks described above in connection with FIG. 1, in dependence on the stimulation success. In the case of side effects and/or of unfavorably positioned electrodes and/or generally with an insufficient stimulation effect, the efficiency of the stimulation can be improved in operation at low stimulus levels by the adaptation of the stimulation breaks. The duration of the stimulation breaks and the duration of the stimulation phases can be regulated with too small a stimulation effect such that a stimulation effect is again adopted.

The stimulation success can in particular be checked by means of a threshold value comparison. Depending on which signals are used for determining the stimulation success, different threshold value comparisons result. If e.g. the pathologically neuronal synchronization is measured via the sensors of the measuring unit 12, e.g. EEG electrodes or deep electrodes (as an LFP signal), experience has shown that the lowering of the synchronization by e.g. at least 20% in comparison with the situation without stimulation is sufficient to determine a sufficient stimulation success. In accordance with an embodiment, an insufficient stimulation success can be determined if the pathologically neuronal synchronization by the application of the stimuli 22 is not reduced by at least a predefined value. If symptoms of the patient are used for determining the stimulation success, which reduction is to be considered as a clinically relevant improvement depends on the kind of clinical parameters used. Such reduction values (e.g. in the sense of the so-called minimal clinically perceptible improvement) are familiar to the skilled person.

Stimulation phases in which the brain and/or spinal cord 25 of the patent is/are stimulated by the stimuli 22 produced by the stimulation unit 11 and stimulation breaks in which no stimuli 22 are applied can be observed in alternating order.

Standard processes of bivariable control can e.g. be used for the regulation of the duration $L_{Stim}$ of the stimulation phases and of the duration $L_{Break}$ of the stimulation breaks. Medical a priori knowledge can, however, also be used, with the lengths $L_{Stim}$ and $L_{Break}$ being increased from a start value in the ($L_{Stim}$, $L_{Break}$) plane with a constant or successively increasing or deterministically and/or chaotically varied increment along a straight line or a bent curve. For example, the ratio $L_{Stim}/L_{Break}$ can increase from $1/n$ to $n$ within the framework of this regulation procedure, where n is, for example, a number in the range from 2 to 10, e.g. 3 or 4 or 5.

FIG. 3 shows a flowchart for an exemplary regulation of the lengths $L_{Stim}$ and $L_{Break}$ of the stimulation phases and stimulation breaks in accordance with a first variant. The lengths $L_{Stim}$ and $L_{Break}$ can, for example, be of equal size during the total process, i.e. $L_{Stim}=L_{Break}=A$ applies. The ratio $L_{Stim}/L_{Break}$ can, however, also be used as the variable for the regulation process. In the latter case, the length $L_{Stim}$ can, for example, differ by up to ±5% or up to ±10%, or up to ±25% from the length $L_{Break}$, i.e. $L_{Stim}=(1+\varepsilon)L_{Break}=A$ applies, where ε in the above-named cases amounts to up to ±0.05 or ±0.1 or ±0.25.

The parameter A is kept constant for so long from a preset starting value until the control and analysis unit 10 classifies the stimulation as unsuccessful. The parameter A is then in particular incrementally increased until the control and analysis unit 10 determines with reference to the measured signals 24 recorded by the measuring unit 12 that the stimulation is again sufficiently successful.

In accordance with an embodiment, the parameter A is increased, in particular incrementally, for so long with a non-sufficient stimulation success until a sufficient stimulation success is determined or an abort criterion is satisfied. The abort criterion should determine when no sufficient stimulation success is to be expected despite a sufficiently large and sufficiently justifiable effort.

The abort criterion can e.g. be satisfied when at least one of a plurality of criteria is satisfied. An abort criterion K1 can e.g. be satisfied if a predefined treatment duration, e.g. of 12 weeks, is exceeded and is otherwise not satisfied. The choice of the predefined treatment duration depends on the respective disease pattern or disease stage and reflects clinical experience.

Figure 4:
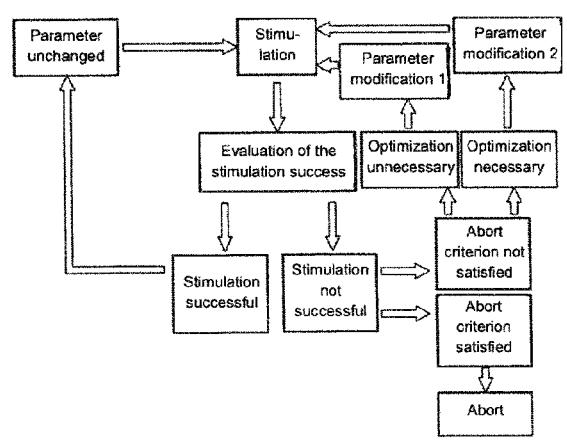
FIG. 4 illustrates a flowchart for illustrating a regulation of the lengths of stimulation phases and stimulation breaks in accordance with a second variant.

FIG. 4 shows a flowchart for a further exemplary regulation of the lengths $L_{Stim}$ and $L_{Break}$ of the stimulation phases and stimulation breaks in accordance with a second variant. The regulation shown in FIG. 4 is in many parts identical to the regulation of FIG. 3, but is more complex in the following respect. It has been found empirically that the regulation shown in FIG. 3 works robustly. A considerable amount of time can, however, typically be saved when—as described above—the ratio $L_{Stim}/L_{Break}$ increases within the framework of the regulation procedure, adapted to the stimulation success, from 1/n to n, where n is, for example, a number in the range from 2 to 10, e.g. 3 or 4 or 5. If this adaptation rule does not work sufficiently, the criterion "optimization required" is satisfied. In this case, the apparatus in accordance with the invention changes to the more robust regulation method shown in FIG. 3. Specifically, the criterion "optimization required" is analog to an abort criterion, i.e. no sufficiently highly pronounced therapeutic success is reached within a specific time or after a specific number of regulation steps.

In accordance with an embodiment, an optimization criterion K2 is satisfied when biomarkers and/or self-evaluation scales, e.g. mental state scales or quality of life scales that are input e.g. via a mobile device (such as an iPhone) and are correspondingly evaluated, measured by means of invasive and/or non-invasive sensors do not improve sufficiently. The sensors of the measuring unit 12 can be used for the invasive sensors used here and/or non-invasive sensors. Different forms of electrodes, e.g. deep electrodes or epicortical electrodes, can in particular be used as invasive sensors. Chronically or intermittently used EEG electrodes or accelerometers can e.g. be used as non-invasive sensors for the detection of characteristic movement patterns such as tremor, akinesia or epileptic fits. A biomarker is e.g. the spectral density in a characteristic frequency region familiar to the skilled person (e.g. the beta band running from approximately 8 to 30 Hz for Parkinson's patients) of the local field potential derived via deep electrodes.

If the biomarker or biomarkers or the self-evaluation scales (i) does/do not fall within a predefined time, e.g. 4 weeks, by a specific percentage from the starting value, e.g. 20% or 50% over a multi-day average depending on the disease or the stage of the disease, and/or (ii) has/have not fallen from the starting value by this percentage after the mth adaptation step of the parameter A, e.g. m=3, the criterion K2 is satisfied in accordance with an embodiment. Otherwise the criterion K2 is not satisfied. In this respect, the adaptation steps of A are constant or successively increasing or are varied deterministically and/or chaotically. The repetition number m corresponds to clinical experience, i.e. the time scale on which the therapeutic success can be adopted with the respective disease.

Instead of the regulations shown in FIGS. 3 and 4, a stimulation can also be carried out in which the lengths $L_{Stim}$ of the stimulation phases and the lengths $L_{Break}$ of the stimulation breaks are constant, i.e. $L_{Stim}=L_{Break}=A$ or $L_{Stim}=(1+\varepsilon)L_{Break}=A$ with ε in the range of ±0.05, ±0.1 or ±0.25, and the stimulation being carried out for so long with a constant A until the stimulation is classified as unsuccessful by the control and analysis unit 10, i.e. until an abort criterion such as described in connection with the regulation in accordance with FIG. 3 is satisfied. The stimulation is then ended. The apparatus 2 can then emit a corresponding message ("stimulation aborted") to the patient, e.g. on a display or by a flashing pilot lamp or the like. This message can also be sent by radio, e.g. as a text message, an email or the like, to the physician. As an alternative to this, the treatment can also be continued on the reaching of the abort criterion; the corresponding message to the patient is then e.g. "please consult physician" and the text message/email is sent to the treating physician to advise him of the insufficient therapy.

The invasive stimulation, e.g. invasive CR stimulation, can be an "open loop" stimulation or a "closed loop" stimulation. In the case of "closed loop" stimulation, implanted sensors of the measuring unit 12, e.g. deep electrodes, epicortical electrodes and/or non-implanted sensors of the measuring unit 12, e.g. chronically or intermittently used EEG electrodes or accelerometers for detecting characteristic movement patterns (tremor, akinesia, epileptic fits) or electrodes for measuring the skin resistance are used to control the stimulation. These sensors can also be used (i) to implement the regulation of the stimulation phases and stimulation breaks, i.e. their adaptation to the therapeutic effect or (ii) to determine optimization or abort criteria such as described above in connection with FIGS. 3 and 4. Different sensors or different signals or different signal components or different dynamic biomarkers (optionally determined from the same starting signals) for the "closed loop" stimulation can also be used for the regulation of the lengths $L_{Stim}$ and $L_{Break}$ of the stimulation phases and stimulation breaks.

The individual components of the apparatus 1 and 2, in particular the control and analysis unit 10, the stimulation unit 11 and/or the measuring unit 12, can be separate from one another in a construction aspect. The apparatus 1 and 2 can therefore also be understood as systems.

The stimulation unit 11 can e.g. be a brain pacemaker and in this case has one or more implantable electrodes, e.g. deep electrodes, as well as optionally connection cables connected therebetween. The electrodes of the stimulation unit 11 typically comprise an insulated electrode shaft and a plurality of stimulation contact surfaces which have been introduced into the electrode shaft.

Figure 5:
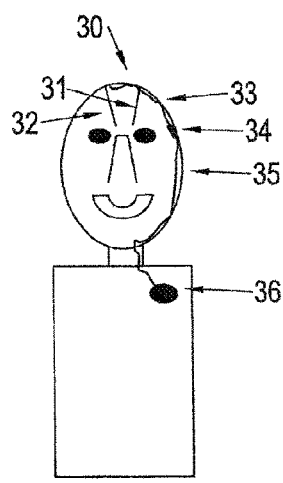
FIG. 5 illustrates a schematic illustration of an apparatus for the electrical stimulation of neurons having a pathologically synchronous and oscillatory neuronal activity.

FIG. 5 schematically shows an apparatus 30 for invasive electrical stimulation of neurons having a pathologically synchronous and oscillatory neuronal activity in accordance with an embodiment of the invention. The apparatus 30 comprises two electrodes 31, 32 that are implanted in the brain of the patient and are connected to a connector 34 via cables 33. The connector 34 is in turn connected to a control and analysis unit 36 via a cable 35. The apparatus 30 can have the functions of the above-described apparatus 1 and 2.

Implantable stimulation units for the optical stimulation of neuronal tissue are known. For example a light source such as a laser. a laser diode or an LED can generate a light beam that is distributed with the help of a light coupling to the inputs of a fiber bundle comprising a plurality of light guides. In this process, a control unit predefines e.g. the point in time at which an individual light pulse or a series of light pulses is coupled into which fiber of the fiber bundle. The decoupling points of the individual fibers of the fiber bundle, i.e. the end of the fibers, lie at different points in the target region in the brain or spinal cord of the patient. The light thus stimulates different sites of the target region in a time sequence predefined by the control unit. Different implantable stimulation units can, however, also be used that are suitable for a direct optical stimulation of neuronal tissue.

The apparatus described herein, in particular the apparatus 1 and 2, can in particular be used for treating neurological or psychiatric diseases, e.g. Parkinson's disease, essential tremor, tremor resulting from multiple sclerosis as well as other pathological tremors, dystonia, epilepsy, depression, locomotor disorders, cerebellar diseases, obsessive compulsive disorders, dementia, Alzheimer's, Tourette's syndrome, autism, functional disorders after stroke, spasticity, tinnitus, sleep disorders, schizophrenia, irritable bowel syndrome, addiction diseases, borderline personality disorder, attention deficit syndrome, attention deficit hyperactivity syndrome, pathological gambling, neuroses, bulimia, anorexia, eating disorders, burnout syndrome, fibromyalgia, migraine, cluster headache, general headache, neuralgia, ataxia, tic disorder or hypertension as well as further diseases which are characterized by pathologically increased neuronal synchronization.

The aforesaid diseases can be caused by a disorder of the bioelectric communication of neural assemblies which are connected in specific circuits. In this respect, a neural ensemble continuously generates pathological neuronal activity and possibly a pathological connectivity associated therewith (network structure). In this respect, a large number of neurons synchronously form action potentials, i.e. the participating neurons fire excessively synchronously. In addition, there is the fact that the pathological neural ensemble has an oscillatory neuronal activity, i.e. the neurons fire rhythmically. In the case of neurological or psychiatric diseases, the mean frequency of the pathological rhythmic activity of the affected neural assemblies lies approximately in the range from 1 to 50 Hz, but can also be outside this range In healthy people, the neurons fire qualitatively differently, however, e.g. in an uncorrelated manner.

In the above-mentioned CR stimulation, a neural ensemble in the brain and/or spinal cord that has a pathologically synchronous and oscillatory neuronal activity is either directly stimulated by the electrical and/or optical stimuli or the stimuli are forwarded to the pathologically active neural ensemble via the nervous system. The stimuli are designed such that the pathologically synchronous activity of the neural ensemble is desynchronized. A lowering of the coincidence rate of the neurons effected by the stimulation can result in a lowering of the synaptic weights and thus in an unlearning of the tendency to produce pathologically synchronous activity.

The stimuli administered in the CR stimulation effect a reset of the phase of neuronal activity of the stimulated neurons in the neural ensemble. The phase of the stimulated neurons is set to or close to a specific phase value, e.g. 0°, independently of the current phase value by the reset (it is not possible in practice to set a specific phase value exactly; however, this is also not required for a successful CR stimulation). The phase of the neuronal activity of the pathological neural ensemble is thus monitored by means of a direct stimulation. Furthermore, the pathological neural ensemble is stimulated by means of a plurality of stimulation contacts of the stimulation unit at different points such that the phase of neuronal activity of the pathological neural ensemble can be reset at the different stimulation points at different points in time. As a result, the pathological neural ensemble whose neurons were previously active synchronously and at the same frequency and phase are split into a plurality of subpopulations. Within each of the subpopulations, the neurons are still synchronous after the resetting of the phase and also still fire at the same pathological frequency, but each of the subpopulations has the phase with respect to their neuronal activity which was enforced by the stimulus generated by the respective stimulation contact. This means that the neuronal activities of the individual subpopulations still have the same pathological frequency, but different phases, after the resetting of their phases into an approximately sinusoidal curve.

Due to the pathological interaction between the neurons, the state with at least two subpopulations generated by the stimulation is unstable and the total neural ensemble fast approaches a state of complete desynchronization in which the neurons fire without correlation. The desired state i.e. the complete desynchronization is thus not immediately present after the time-offset (or phase-shifted) application of the phase-resetting stimuli, but is usually adopted within a few periods or even in less than one period of the pathological frequency.

Figure 6:
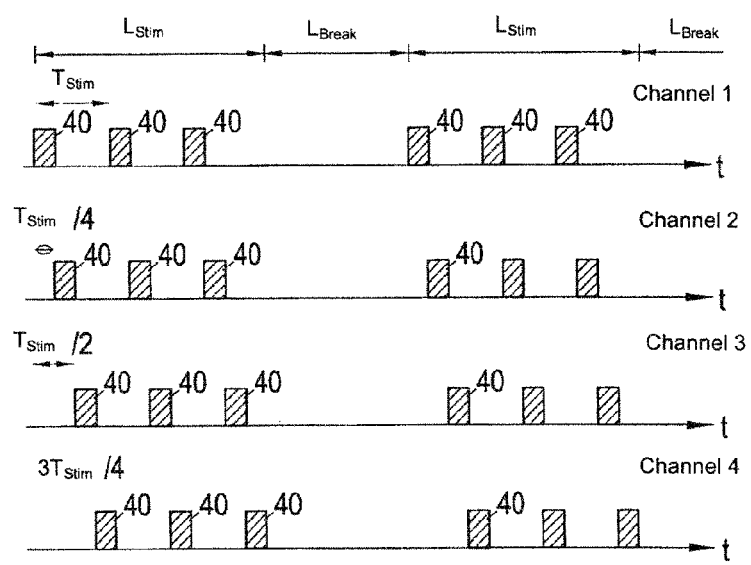
FIG. 6 illustrates a schematic representation of a CR stimulus sequence for stimulating a neural ensemble.
Figure 7:
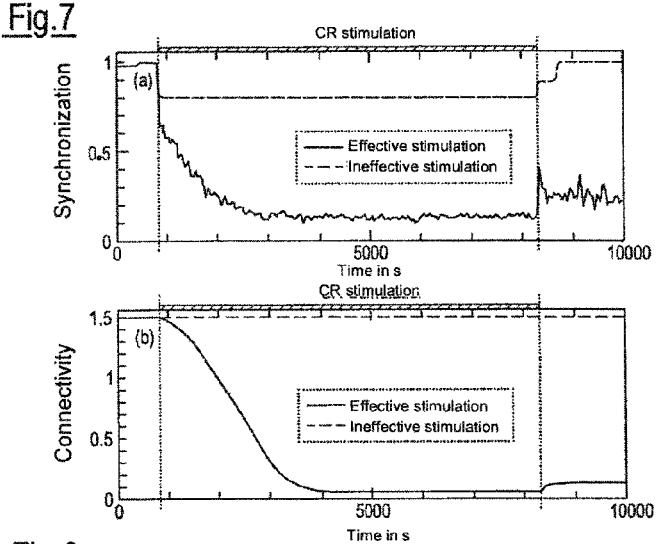
FIG. 7 illustrates graphs for illustrating an effective and an ineffective CR stimulation.
Figure 8:
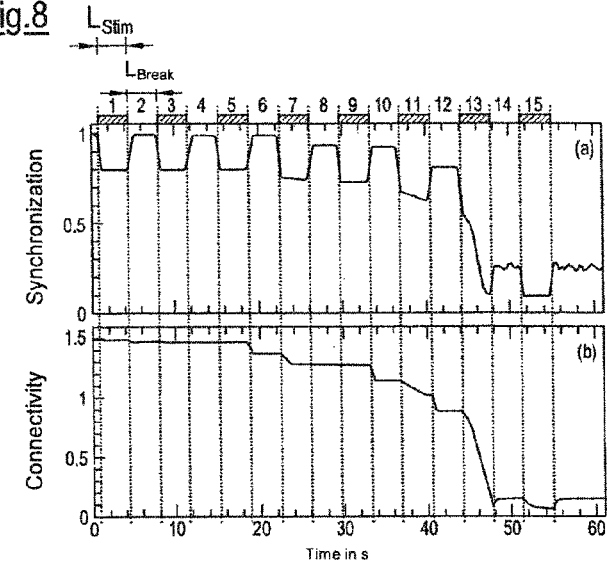
FIGS. 8 to 12 illustrate graphs for illustrating CR stimulations having different stimulation phase lengths and stimulation break lengths.

FIG. 6 shows an example of a CR stimulation with a total of four channels. A subpopulation of the pathological neural ensemble is stimulated over each of the four channels. In each of the four channels, electrical and/or optical stimuli 40 are applied in a sequence periodically with the period $T_{Stim}$, where $T_{Stim}$ is here also close to the middle period of the pathological oscillation of the neural ensemble or deviates from the textbook value by up to ±5%, ±10% or ±20% (typically fstim=$1/T_{Stim}$ lies in the range from 1 to 30 Hz). The stimuli 40 effect a phase reset of the neuronal activity of the respective stimulated subpopulation. The time delay between the sequences of adjacent channels furthermore amounts to $T_{Stim}/4$, since four channels are present. For the general case of N channels, the time delay of adjacent channels would amount to $T_{Stim}/N$ (it is also possible to deviate from this value by e.g. up to ±5%, ±10% or ±20%). Furthermore, the sequence of the stimulus administration over the N channels does not have to be identical in each stimulation cycle, but can e.g. also be varied in a randomized manner from stimulation cycle to stimulation cycle.

Furthermore, the lengths $L_{Stim}$ of the stimulation phases and the lengths $L_{Break}$ of the stimulation breaks are shown that can be set or regulated as described above. It must be noted that in FIG. 6, the lengths $L_{Stim}$ and $L_{Break}$ and the lengths of the phase-reset stimuli 40 are not reproduced true to scale.

It must be pointed out that breaks in which no stimuli are applied can also be observed in conventional stimulation methods. For example, in CR stimulation, stimulation can take place for n cycles and no stimulation can take place for the following m cycles and this stimulation pattern can be periodically continued, where n and m are small whole numbers. Such breaks can also be observed in accordance with the invention during the stimulation phases of the length $L_{Stim}$. The stimulation breaks in accordance with the invention of the length $L_{Break}$, however, differ from the breaks during the stimulation phases in that they are only observed when it was previously found that the stimulation success achieved by the stimulation is not sufficient and/or if side effects occur and/or if the stimulation unit is unfavorably positioned in the body of the patient.

Different stimulation forms instead of CR stimulation can also be used provided that long-lasting therapeutic effects can be achieved with these stimulation forms in the desynchronization of pathologically active neural ensembles.

The effects achievable using the invention described herein are illustrated with reference to simulation results in FIGS. 7 to 13.

In FIGS. 7(a) and 7(b), the degree of synchronization and the synaptic connectivity of a neural ensemble having a pathologically synchronous and oscillatory neuronal activity are shown before, during and after a CR stimulation. The horizontal bars drawn at the top in both representations indicate the time period in which the CR stimulation is applied.

As FIGS. 7(a) and 7(b) show, an effective CR stimulation effects a fast desynchronization of the neural ensemble and a fast reduction in the connectivity. However, under certain circumstances, only a small stimulation success can arise, which can be seen from the fact that the degree of synchronization and the connectivity within the stimulated neural ensemble only reduce slightly despite the CR stimulation.

The efficiency of the CR stimulation can be improved with the above-described apparatus 1 and 2 by the insertion of stimulation breaks at low stimulus levels. Stimulation breaks can furthermore be added, e.g. in the case of unfavorably positioned electrodes and/or of side effects to allow an efficient stimulation at low stimulation levels.

An unfavorably positioned electrode is an electrode in which too many of the stimulation contacts are ineffective. An electrode is in particular evaluated as unfavorably positioned when so many stimulation contacts of the electrode are ineffective that at least 3 effective stimulation contacts are no longer present. A stimulation contact is inefficient if a stimulation by an ensemble of individual stimuli over the respective stimulation contact does not result in a phase reset of the pathological synchronous oscillation (in comparison with the prestimulus baseline) or in which a periodic stimulation does not result in a sufficiently high n:m phase synchronization between the periodic stimulus and the synchronous oscillation.

Side effects depend on the respective disease and on the respectively selected target region. Dyskinesias can occur e.g. as a side effect of displaced electrodes that present by a coactivation (instead of an alternating activation) of antagonistic muscles (e.g. flexors and extensors). Side effects can also present by a stimulation-dependent increase in synchronous activity in corresponding sensors.

FIGS. 8(a) and 8(b) show the results of a stimulation that comprises alternating stimulation phases in which a CR stimulation is carried out and stimulation breaks in which no stimulation is carried out. The stimulation phases are drawn by horizontal bars in FIGS. 8(a) and 8(b). The lengths $L_{Stim}$ and $L_{Break}$ of the stimulation phases and stimulation breaks are of equal length and respectively amount to 3,600 s in the present example. Except for the stimulation breaks, the same stimulation parameters were used for the simulations shown in FIGS. 8(a) and 8(b) as for the simulation of the ineffective simulation shown in FIGS. 7(a) and 7(b). The insertion of the stimulation breaks produces a clear reduction in the degree of synchronization and in the connectivity. The insertion of the stimulation breaks consequently has the effect that an otherwise ineffective stimulation is effective. Furthermore, long-lasting therapeutic effects can be achieved with this form of stimulation. The degree of synchronization and the connectivity also remain at a very low level after the complete switching off of the stimulation.

It is important for the success of the form of stimulation in accordance with the invention to determine suitable lengths $L_{Stim}$ and $L_{Break}$ for the stimulation phases and stimulation breaks. FIGS. 9 to 12 show the results of different simulations for which different values for $L_{Stim}$ and $L_{Break}$ were used with otherwise the same stimulation parameters. The values are shown in the following table.

Figure 9:
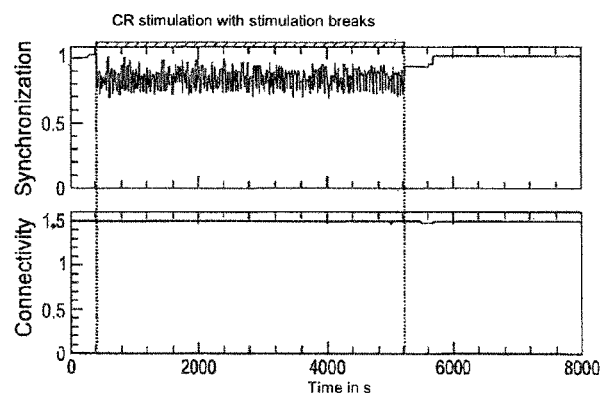
Figure 10:
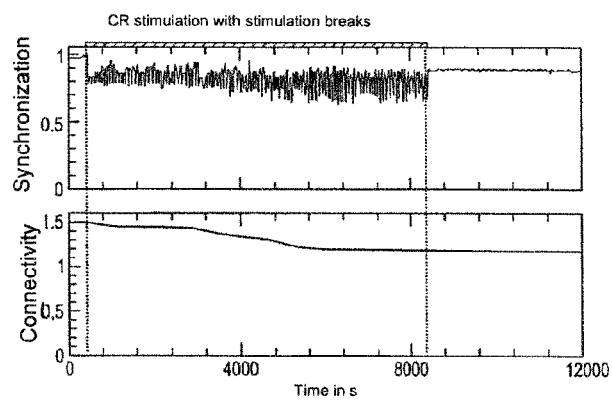
Figure 11:
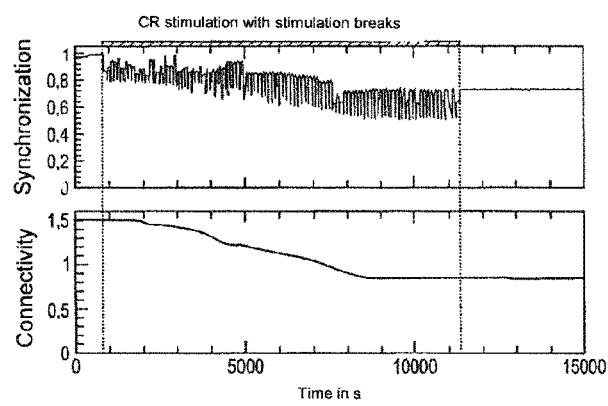
Figure 12:
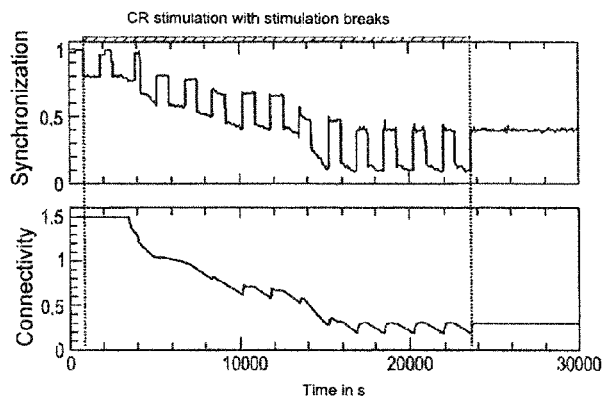

|  | $L_{Stim}$ | $L_{Break}$ |
| --- | --- | --- |
| FIG. 9 | 24 s | 24 s |
| FIG. 10 | 24 s | 56 s |
| FIG. 11 | 24 s | 80 s |
| FIG. 12 | 960 s | 720 s |

In FIGS. 9 to 12, those time periods are marked by the horizontal bars in which the CR stimulation in accordance with the invention is carried out with mutually alternating stimulation phases and stimulation breaks.

For only very brief stimulation phases and stimulation breaks, only a very small effect is produced (cf. FIG. 9) that is furthermore of only brief duration after the ending of the stimulation process. Better results are achieved when, with an unchanging length $L_{Stim}$ of the stimulation phases, the length $L_{Break}$ of the stimulation breaks is increased (cf. FIGS. 10 and 11). The best results are achieved in the simulations shown here for relatively large values of several minutes for the lengths $L_{Stim}$ and $L_{Break}$ (cf. FIG. 12).

In FIG. 13, the results of different CR stimulations in accordance with the invention are shown in an ($L_{Stim}$/$L_{Break}$) plane. The circular symbols show ineffective stimulations; all the other symbols represent effective stimulations. Furthermore the ($L_{Stim}$/$L_{Break}$) plane in FIG. 12 is divided by a line into a region of ineffective stimulation and a region of effective stimulation. As can be seen from FIG. 12, stimulations having only short values for $L_{Stim}$ and $L_{Break}$ as well as stimulations in which $L_{Stim}$ is too long in comparison with $L_{Break}$ are ineffective. The best stimulation results were achieved for parameter values from the top right region of the ($L_{Stim}$/$L_{Break}$) plane.

The invention claimed is:

1. An apparatus for suppressing a pathologically synchronous and oscillatory neuronal activity, the apparatus comprising
a stimulation unit implantable in a patient for stimulating neurons, using at least one of electrical or optical stimuli, in at least one of a brain and spinal cord of the patient that demonstrate a pathologically synchronous and oscillatory neuronal activity, wherein the electrical or optical stimuli are adapted to suppress the pathologically synchronous and oscillatory neuronal activity upon administration to the patient;
a measuring unit for recording measured signals that reproduce a neuronal activity of the stimulated neurons; and a control and analysis unit for controlling the stimulation unit and for analyzing the measured signals, wherein the control and analysis unit is configured to perform actions comprising:
  i) control the stimulation unit to apply the at least one of electrical or optical stimuli at a frequency of at least 1 Hz with a stimulation break following application of the electrical or optical stimuli;
  ii) determine a level of reduction in either a) the pathologically synchronous and oscillatory neuronal activity or b) a symptom related to the pathologically synchronous and oscillatory neuronal activity using the measured signals recorded in response to the application of the electrical or optical stimuli;
  iii) when the level of reduction does not achieve a threshold value, extend a duration of the stimulation break, wherein no stimuli are applied during the stimulation break that can suppress the pathologically synchronous and oscillatory neuronal activity, wherein a length of the stimulation break is at least 50 second; and
  iv) repeat actions i) to iii) at least once until termination.

2. The apparatus in accordance with claim 1, wherein the control and analysis unit is furthermore configured such that it repeatedly extends the duration of the stimulation break during a plurality of cycles of actions i) to iii) until the control and analysis unit determines that the level of reduction has achieved the threshold value or until an abort criterion is satisfied.

3. The apparatus in accordance with claim 2, wherein the control and analysis unit is configured to extend the duration of the stimulation break incrementally.

4. The apparatus in accordance with claim 2, wherein the control and analysis unit is furthermore configured to extend a duration of phases of the electrical or optical stimuli in addition to the duration of the stimulation break until the control and analysis unit determines that the level of reduction has achieved the threshold value or the abort criterion is satisfied.

5. The apparatus in accordance with claim 4, wherein the control and analysis unit is configured to extend the duration of the phases of the electrical or optical stimuli incrementally.

6. The apparatus in accordance with claim 1,
  wherein the phases of the electrical or optical stimuli each have a duration $L_{Stim}$ and the stimulation break observed between mutually following stimulation phases has a duration $L_{Break}$, wherein a parameter A is defined as either $A=L_{Stim}=L_{Break}$, when $L_{Stim}=L_{Break}$, or otherwise as $A=L_{Stim}/L_{Break}$, and
  wherein the control and analysis unit is furthermore configured to either increase A if the level of reduction does not achieve the threshold value or increase A incrementally if the level of reduction does not achieve the threshold value or until an abort criterion is, satisfied.

7. The apparatus in accordance with claim 6, wherein the control and analysis unit is furthermore configured to either increase A for $A=L_{Stim}/L_{Break}$ from $1/n$ to n if the level of reduction does not achieve the threshold value or increase A for $A=L_{Stim}/L_{Break}$ from $1/n$ to n incrementally if the level of reduction does not achieve the threshold value.

8. The apparatus in accordance with claim 7, where n is a number in a range from 2 to 10.

9. The apparatus in accordance with claim 8, wherein the control and analysis unit is furthermore configured to keep A constant until the control and analysis unit determines that the level of reduction does not achieve the threshold value.

10. The apparatus in accordance with claim 6, wherein the control and analysis unit is furthermore configured to increase A when the level of reduction does not achieve the threshold value until the control and analysis unit determines that the level of reduction has achieved the threshold value or until the abort criterion is satisfied.

11. The apparatus in accordance with claim 4, wherein the stimulation unit is configured to perform a coordinated reset stimulation during the phases of the electrical or optical stimuli, with phases of neuronal activity of a plurality of subpopulations of a stimulated neural ensemble having a pathologically synchronous and oscillatory neuronal activity being reset at different points in time.

12. The apparatus in accordance with claim 1, wherein the duration of the stimulation break is at least 3 minutes.

13. The apparatus in accordance with claim 1, wherein the duration of the stimulation break corresponds to a duration of at least 200 or at least 1,000 periods of the pathologically synchronous and oscillatory neuronal activity.

14. A method for suppressing a pathologically synchronous and oscillatory neuronal activity, the method comprising:
  i) applying a stimuli, by a stimulation unit implantable into a patient and at a frequency of at least 1 Hz with a stimulation break following the application of the stimuli, to neurons in at least one of a brain and a spinal cord of the patient that demonstrate a pathologically synchronous and oscillatory neuronal activity, wherein the stimuli is at least one of an electrical stimuli or an optical stimuli, wherein the stimuli are adapted to suppress the pathologically synchronous and oscillatory neuronal activity on an administration to the patient; and
  ii) when at least one of the following is determined a) the stimuli does not achieve a threshold value for a level of reduction in either the pathologically synchronous and oscillatory neuronal activity or a symptom related to the pathologically synchronous and oscillatory neuronal activity, b) side effects occur to the patient, or c) the stimulation unit is unfavorably positioned in the body of the patient, then extending a duration of the stimulation break, with no stimuli being applied during the stimulation break that could suppress the pathologically synchronous and oscillatory neuronal activity, wherein a length of the stimulation break is at least 50 seconds; and
  iii) repeating i) and ii) at least once until termination.

15. The method in accordance with claim 14, further comprising:
  recording measured signals that reproduce a neuronal activity of the stimulated neurons; and
  checking the level of reduction with reference to the measured signals recorded in response to the application of the stimuli.

16. The method in accordance with claim 14, further comprising extending the duration of the stimulation break until the level of reduction has achieved the threshold value or until an abort criterion is satisfied.

17. The method in accordance with claim 16, further comprising incrementally extending the duration of the stimulation break.

18. The method in accordance with claim 16, further comprising extending a duration of stimulation phases of the stimuli, in addition to the extending of the duration of the stimulation break, until the level of reduction has achieved the threshold value or until the abort criterion is satisfied.

19. The method in accordance with claim 18, further comprising incrementally extending the duration of the stimulation phases.

20. The method in accordance with claim 14,
wherein stimulation phases each have a duration $L_{Stim}$ and the stimulation break observed between mutually following stimulation phases has a duration $L_{Break}$, wherein a parameter A is defined as either $A=L_{Stim}=L_{Break}$, when $L_{Stim}=L_{Break}$, or otherwise as $A$ $L_{Stim}/L_{Break}$, and
wherein the method further comprises either a) increasing A when at least one of the level of reduction does not achieve the threshold value, side effects occur to the patient, or the stimulation unit is unfavorably positioned in the patient, or b) increasing A incrementally when at least one of the level of reduction does not achieve the threshold value, side effects occur to the patient, or the stimulation unit is unfavorably positioned in the body of the patient.

* * * * *